(12) United States Patent
Fukuhara

(10) Patent No.: US 6,606,577 B1
(45) Date of Patent: Aug. 12, 2003

(54) METHOD AND SYSTEM FOR MEASURING FLICKER SENSITIVITY DISTRIBUTION, AND COMPUTER-READABLE RECORDING MEDIUM STORING FLICKER SENSITIVITY DISTRIBUTION MEASURING PROGRAM

(76) Inventor: Jun Fukuhara, 1-19, Gakuen-Minami 2-chome, Nara-shi, Nara-ken (JP)

(*) Notice: Subject to any disclaimer, the term of this patent is extended or adjusted under 35 U.S.C. 154(b) by 0 days.

(21) Appl. No.: 09/319,899
(22) PCT Filed: Oct. 16, 1998
(86) PCT No.: PCT/JP98/04681
§ 371 (c)(1),
(2), (4) Date: Jun. 14, 1999
(87) PCT Pub. No.: WO99/20180
PCT Pub. Date: Apr. 29, 1999

(30) Foreign Application Priority Data

Oct. 16, 1997 (JP) .............................. 9-303739

(51) Int. Cl.[7] ................................. A61B 3/02
(52) U.S. Cl. ..................... 702/127; 702/183; 351/243
(58) Field of Search ............................ 702/127, 75, 79, 702/19, 108, 150, 182, 183, 189, FOR 170, FOR 171, FOR 103, FOR 104, FOR 107, FOR 115, FOR 131, FOR 134, FOR 135, FOR 141, FOR 144; 351/200, 239, 243, 246, 224, 201, 205, 211; 600/558, 300

(56) References Cited

U.S. PATENT DOCUMENTS

| | | | | |
|---|---|---|---|---|
| 4,324,460 A | * | 4/1982 | Daley | 351/243 |
| 5,717,481 A | * | 2/1998 | Obata et al. | 351/224 |
| 6,113,537 A | * | 9/2000 | Castano | 600/300 |

FOREIGN PATENT DOCUMENTS

| | | |
|---|---|---|
| EP | 0 497 648 A1 | 8/1992 |
| JP | 10-24017 | 3/1979 |
| JP | 10-24017 * | 1/1998 |
| JP | 55-142107 | 1/1998 |
| WO | 91/14399 | 10/1991 |

OTHER PUBLICATIONS

Isono et al., Translation of JP 10–24017, Mar. 2002, pp. 1–19.*

Fuchi et al., "Fundus–Controlled Flicher Perimetry" *Ophthalmology of the New Age* (in Japanese), vol. 12, No. 7, (Japan), K.K. Medical Aoi Shuppan (Jul. 30, 1995) pp 1111–1114, particularly Fig. 4 and related description.

Ayani et al., "Flicker perimetry using a personal computer," *Rinsho Ganka (Jpn J Clin Ophthalmol)*, vol. 52, No. 6, pp. 1082–1085 (1998). (No month).

Fukuda et al., "Shikiichi to sono Sokuteihou (in Japanese)," Neuro–opthahnol, vol. 7, No. 3 pp. 291–298 (1990). (No month).

Iuchi et al., "Fundus–Controlled Flicker Perimetry," pp. 1–6, English–language translation of "Fundus–Controlled Flicker Perimetry," vol. 12, No. 7, K.K. Medical Aoi Shuppan (Jul. 30, 1995), pp. 1111–1114, particularly Fig. 4 and related description.

* cited by examiner

*Primary Examiner*—Hal Wachsman

(57) ABSTRACT

A flicker sensitivity distribution measuring method is provided to maintain a subject in a fixation state and to accurately measure flicker sensitivity distribution. The sensitivity distribution measuring method includes the steps of displaying a target on a screen of a display while changing high and low luminances of a flickering target stepwise so that the average of the high luminance and the low luminance in each cycle of flickering of the target is always equal to the luminance of the screen serving as a background for the target, and determining a flicker sensitivity on the basis of the high luminance and the low luminance in one cycle of flickering of the target at a moment when the target is perceived.

5 Claims, 7 Drawing Sheets

|   | X | Y |
|---|---|---|
| C1 | $X_1$ | $Y_1$ |
| C2 | $X_2$ | $Y_2$ |
| C3 | $X_3$ | $Y_3$ |
| C4 | $X_4$ | $Y_4$ |
| C5 | $X_5$ | $Y_5$ |
| C6 | $X_6$ | $Y_6$ |
| C7 | $X_7$ | $Y_7$ |
| C8 | $X_8$ | $Y_8$ |
| C9 | $X_9$ | $Y_9$ |
| C10 | $X_{10}$ | $Y_{10}$ |

14a, 14b

|   | X | Y |
|---|---|---|
| C11 | $X_{11}$ | $Y_{11}$ |
| C12 | $X_{12}$ | $Y_{12}$ |
| C13 | $X_{13}$ | $Y_{13}$ |
| C14 | $X_{14}$ | $Y_{14}$ |
| C15 | $X_{15}$ | $Y_{15}$ |
| C16 | $X_{16}$ | $Y_{16}$ |
| C17 | $X_{17}$ | $Y_{17}$ |
| C18 | $X_{18}$ | $Y_{18}$ |
| C19 | $X_{19}$ | $Y_{19}$ |
| C20 | $X_{20}$ | $Y_{20}$ |

|   | X | Y |
|---|---|---|
| C21 | $X_{21}$ | $Y_{21}$ |
| C22 | $X_{22}$ | $Y_{22}$ |
| C23 | $X_{23}$ | $Y_{23}$ |
| C24 | $X_{24}$ | $Y_{24}$ |
| C25 | $X_{25}$ | $Y_{25}$ |

| Hz1 |
|-----|
| Hz2 |
| Hz3 |
| Hz4 |

| Imax9 | Imin9 |
|-------|-------|
| Imax8 | Imin8 |
| Imax7 | Imin7 |
| Imax6 | Imin6 |
| Imax5 | Imin5 |
| Imax4 | Imin4 |
| Imax3 | Imin3 |
| Imax2 | Imin2 |
| Imax1 | Imin1 |
| Imax0 | Imin0 |

FIG.5C

METHOD AND SYSTEM FOR MEASURING FLICKER SENSITIVITY DISTRIBUTION, AND COMPUTER-READABLE RECORDING MEDIUM STORING FLICKER SENSITIVITY DISTRIBUTION MEASURING PROGRAM

TECHNICAL FIELD

The present invention relates to a flicker sensitivity distribution measuring method for testing the visual function of a subject, a system for carrying out the flicker sensitivity distribution measuring method, and a computer-readable recording medium storing a flicker sensitivity distribution measuring program.

BACKGROUND ART

There has been a known flicker sensitivity measuring method for testing the visual function of a subject. This known flicker sensitivity measuring method makes a target flicker at predetermined positions in the subject's visual field, determines temporal modulation sensitivity by testing whether or not the subject's eye in the state of fixation is able to perceive the flickering target, and represents the visual functions of the retina for those positions by numerical values. Flicker sensitivity measuring systems have been proposed to carry out the known flicker sensitivity measuring method. One of the flicker sensitivity measuring systems has a background dome provided with a plurality of light emitting diodes as targets embedded therein at predetermined positions, and makes the light emitting diodes flicker by electrical modulation to indicate flickering targets on the background dome. Another known flicker sensitivity measuring system has a sector disk or a polarizing plate at positions on an optical path between a light source and the subject's eye, rotates the sector disk or the polarizing plate for mechanical modulation to indicate flickering targets on a concave surface of a background dome.

DISCLOSURE OF THE INVENTION

Since the conventional flicker sensitivity measuring system turns on light emitting diodes or the like placed in the visual field or project a light beam into the visual field, the subject perceives the target before the subject perceives flickering of the target. When a target appears in a part of a monotone visual field of a uniform luminance, the luminance of the part is equal to the sum of the respective luminances of the background and the target. Therefore, the target is brighter than the background, and the subject perceives the target before the subject perceives flickering of the target. Consequently, when the conventional flicker sensitivity measuring system is used for flicker sensitivity measurement, the subject is always able to perceive the target before deciding whether or not the target is flickering.

If flicker sensitivity is measured under such condition, the subject's visual line supposed to be fixed is affected by a target appeared in the visual field to cause the subject's visual line to move to a position where the target appears. Consequently, accurate measurement of flicker sensitivity distribution cannot be achieved. Since the subject's visual line supposed to be fixed moves to a position where the target appears every time the target appears in the visual field, the subject is compelled unavoidably to concentrate attention on the target, is unable to maintain stable fixation and is liable to be tired. Since flicker sensitivity test using many flickering targets shown at different positions takes a long time, the subject is tired and the tired subject's flicker sensitivity is measured, which reduces the reliability of measured data.

The inventor of the present invention hit on an idea that the subject is able to perceive a flickering target with the subject's eye remaining in the state of fixation if the target is presented so that the subject is able to become aware of the existence of the target in the visual field only when the subject perceives the flickering target. The inventor of the present invention studied technical problems, and conducted experiments to realize this idea, and have acquired a very interesting knowledge that, when the average of a luminance of a flickering target when the target is bright (hereinafter referred to as "high luminance") and a luminance of the flickering target when the target is dark (hereinafter referred to as "low luminance") is equal to the luminance of a background, a subject incapable of perceiving flickers resulting from the alternate repetition of the high luminance and the low luminance takes the average luminance of the high luminance and the low luminance of the target, i.e., the luminance equal to that of the background, as the luminance of the target and is unable to perceive the target presented in the visual field.

The present invention solves the technical problems by the following means.

According to a first aspect of the present invention, a flicker sensitivity distribution measuring method comprises the steps of: displaying a flickering target on the screen of a display while changing the high luminance and the low luminance of the flickering target stepwise so that the average of the high luminance and the low luminance in each cycle of flickering of the target is always equal to the luminance of the screen serving as a background of the target; and determining a flicker sensitivity on the basis of a high luminance and a low luminance in one cycle of flickering of the target at a moment when the target is perceived.

According to a second aspect of the present invention, a flicker sensitivity distribution measuring system comprises: a stand for fixedly holding the face of a subject; a display disposed with its screen facing the stand; a controller for controlling the display to display a flickering target on the screen of the display and determining a flicker sensitivity when the flickering target is perceived; and a target perception indicating unit which provides a target perception signal representing the perception of the flickering target; wherein the controller comprises a luminance data storing means storing data on luminance sets of different levels each of a high luminance and a low luminance of the target in one cycle of flickering determined so that the average of the high luminance and the low luminance is always equal to the luminance of the screen serving as a background of the target; a position data storing means storing a plurality of sets of coordinates indicating positions for the target; and an arithmetic means for determining a flicker sensitivity on the basis of a high luminance and a low luminance of the target in one cycle of flickering of the target at a moment when the target is perceived upon the reception of a target perception signal from the target perception indicating unit; and wherein the controller reads sequentially the luminance sets of different levels each of a high luminance and a low luminance of the target in one cycle of flickering from the luminance data storing means; reads sequentially the plurality of sets of coordinates indicating positions for the target from the position data storing means; displays the flickering target at each of positions on the screen while changing the high luminance and the low luminance of the flickering target stepwise at each position.

According to a third aspect of the present invention, a computer-readable recording medium storing a flicker sensitivity distribution measuring program for making a computer the sequences of: displaying a flickering target on the screen of a display while changing the high luminance and the low luminance of the flickering target so that the average of the high luminance and the low luminance in each cycle of flickering of the target is always equal to the luminance of the screen serving as a background of the target; and determining a flicker sensitivity on the basis of a high luminance and a low luminance of one cycle of flickering of the target at a moment when the target is perceived.

According to any one of the first to the third aspect of the present invention, it is preferable to determine the flicker sensitivity by calculating a modulation threshold on the basis of a high luminance and a low luminance in one cycle of flickering of the target at a moment when the target is perceived, and to convert the modulation threshold into a corresponding value in decibel.

According to the first to the third aspect of the present invention, the target is made to flicker in a high luminance and a low luminance so that the average of the high luminance and the low luminance in each cycle of flickering is equal to the luminance of the screen to make a subject perceive the flickering target. Therefore, the subject is unable to perceive the target while the subject is unable to perceive flickering of the target, and the subject is able to perceive the target in the visual field only when the subject perceives flickering of the target. Accordingly, the subject is able to maintain a fixation state easily and surely and hence the flicker sensitivity distribution can accurately be measured without making the subject tired.

Since the flickering target is displayed on the screen of the display and the high luminance and the low luminance of the flickering target are changed stepwise, and a flicker sensitivity is determined on the basis of a high luminance and a low luminance of one cycle of flickering of the target at a moment when the target is perceived. An accurate flicker test can quickly be achieved.

The present invention is applicable not only to a flicker test, but also to the determination of a frequency harmonious with the color of a background by using a target of a color different from that of the background or to a test for determining the wavelength of a color that causes Rayleigh equation.

Thus, the present invention has high industrial utility.

BRIEF DESCRIPTION OF THE DRAWINGS

FIGS. 5A to 5C are diagrammatic views of the respective organizations of data stored in memories included in a storage unit shown in FIG. 4;

BEST MODE FOR CARRYING OUT THE INVENTION

Preferred embodiments of the present invention will be described hereinafter with reference to the accompanying drawings.

Figure 1:
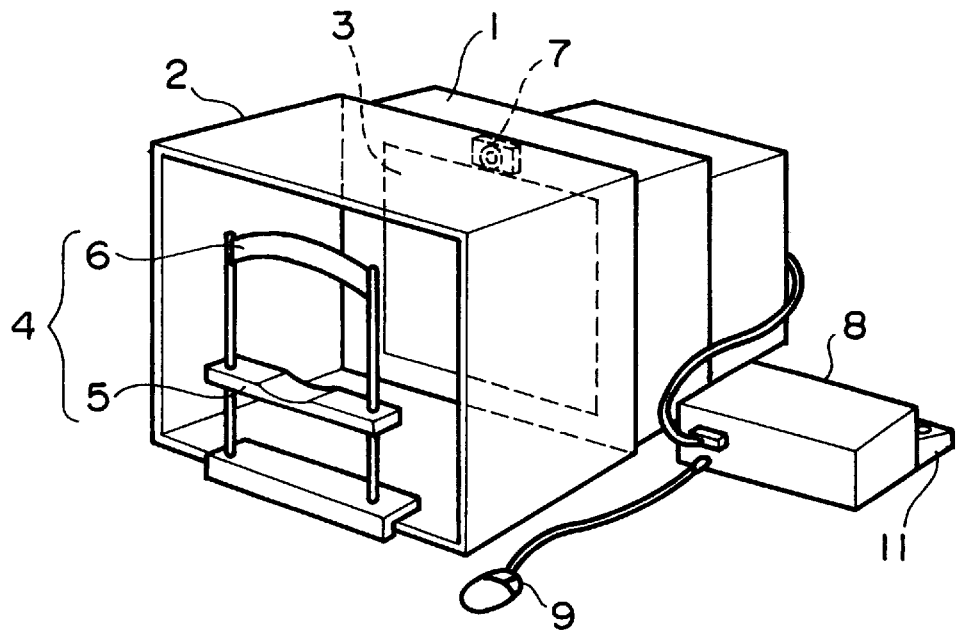
FIG. 1 is a perspective view of a flicker sensitivity distribution measuring system in a preferred embodiment according to the present invention.
Figure 2:
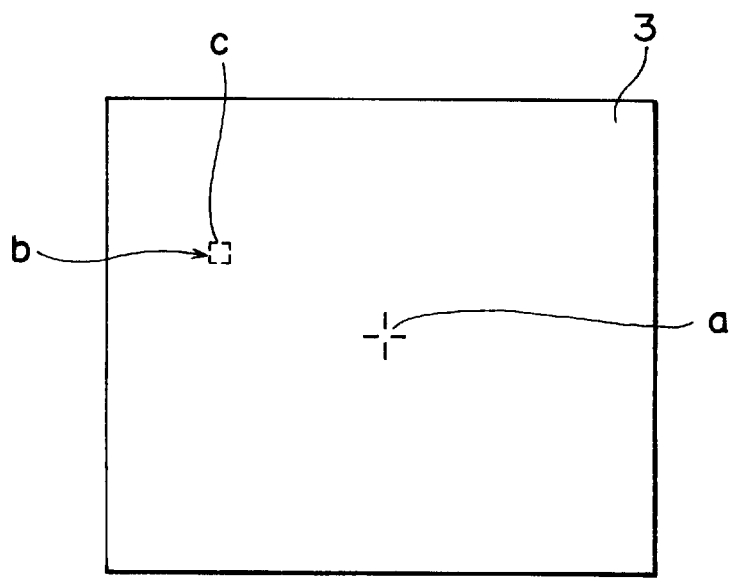
FIG. 2 is a front view of the screen of a display included in the flicker sensitivity distribution measuring system shown in FIG. 1 of assistance in explaining targets displayed on the screen.
Figure 3:
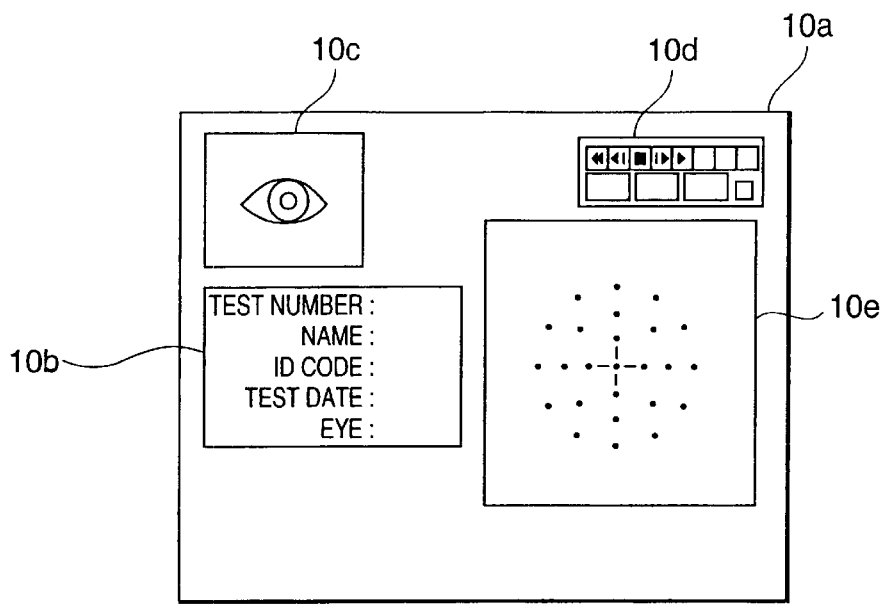
FIG. 3 is a front view of a monitor screen (monitor display) for monitoring the fixation of a subject during the operation of the flicker sensitivity distribution measuring system by a tester.

Referring to FIG. 1, there are shown a display 1 having a screen (background) 3 to display a flickering target thereon, a shading box 2 having the shape of a rectangular pipe and surrounding the screen 3 of the display 1, and a stand 4 disposed at an open end of the shading box 2 to support the face of a subject fixedly in place. The stand 4 has a chin support 5 on which the subject's chin rests, and a forehead support 6 against which the subject's forehead rests. The chin support 5 can vertically be moved. An infrared television camera 7 is attached to a middle part of an upper member of the frame of the display 1 to monitor the fixation state of the subject by taking a picture of the subject's face. The display 1 and the infrared television camera 7 are connected to a controller 8 disposed near the display 1. A target perception indicating device 9, which is operated by the subject to inform the controller 8 of the perception of a flickering target, a monitor display 10 (FIG. 4) to display a monitor picture 10a (FIG. 3), and an operating unit 11 to be operated by a tester to measure the subject's flicker sensitivity are connected to the controller 8. The tester operates the operating unit 11, watching the monitor picture 10a displayed on the monitor display 10. As shown in FIG. 3, the monitor picture 10a displayed on the monitor display 10 includes an information window 10b indicating information about the subject including data on the test number, subject's name, ID code, test date, and subject's eyes; a fixation monitoring window 10c for monitoring the state of eye fixation of the subject; icons 10d representing measuring functions; and a display screen window 10e to display flicker sensitivities at different positions. As shown in FIG. 2, a fixation target a and a target b are displayed on the screen 3 of the display 1. In FIG. 2, indicated at c is a position where the target b is displayed.

Figure 4:
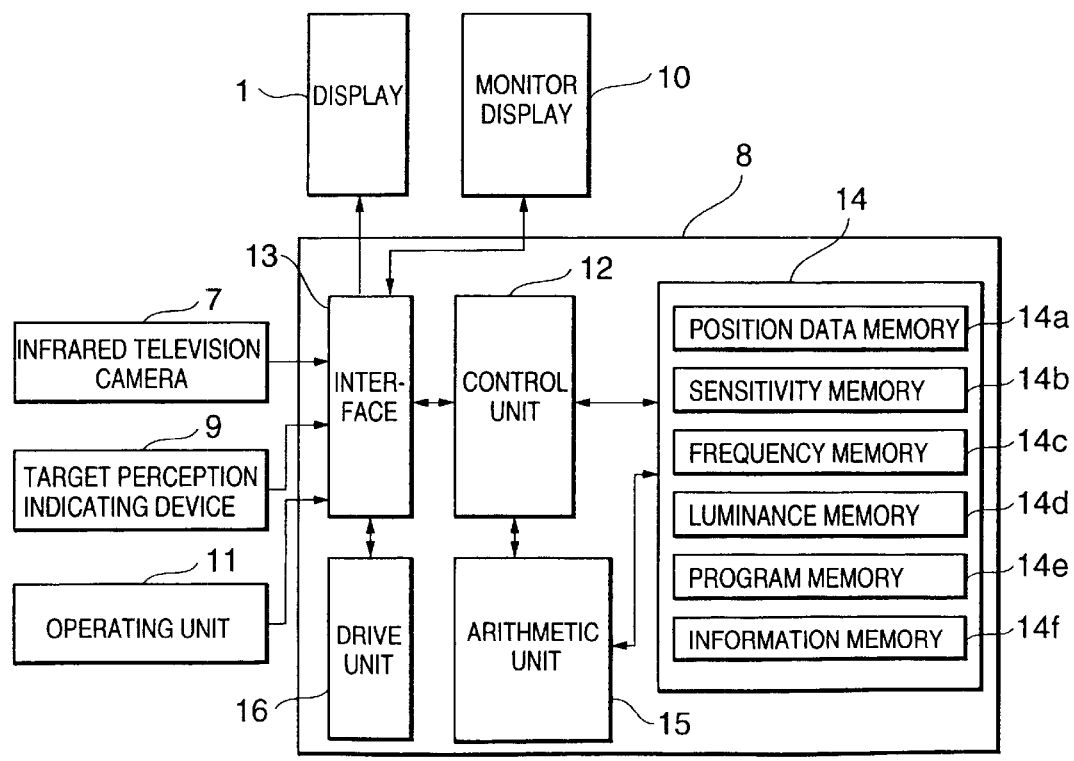
FIG. 4 is a block diagram of the flicker sensitivity distribution measuring system shown in FIG. 1.
Figure 6:
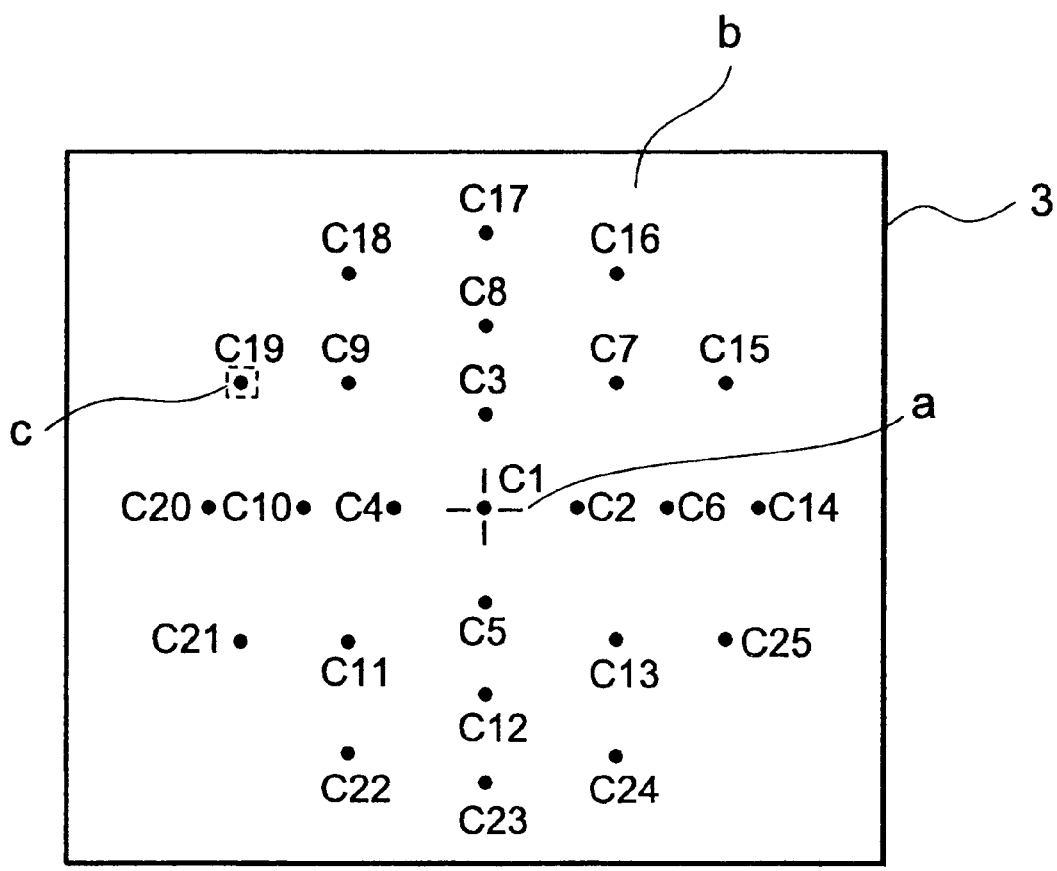
FIG. 6 is a front view of the screen shown in FIG. 2 of assistance in explaining positions where targets are displayed.

Referring to FIG. 4, the controller 8 comprises a control unit 12 which executes commands to control the flow of data, and an I/O interface 13 connecting the control unit 12 to the peripheral devices including the display 1, the infrared television camera 7, the target perception indicating device 9, the monitor display 10 and the operating unit 11. The controller 8 further comprises a storage unit 14 storing information about the subject, data specifying operations to display the fixation target a and the target b on the display 1, a flicker sensitivity distribution measuring program and such, an arithmetic unit (arithmetic means) 15 which receives a target perception signal (a signal provided by the subject upon the perception of the flickering target b) from the target perception indicating device 9 and calculates a flicker sensitivity on the basis of data on a high luminance and a low luminance in one cycle of flickering of the target at a moment when the target is perceived, and a drive unit 16 which drives a recording medium to write data to the recording medium and to read data from the recording medium.

As shown in FIG. 4, the control unit 12 executes control operations to store information provided by the tester by operating the operating unit 11 in the storage unit 14 and to display the same in the information window 10b of the monitor picture 10a. Upon the reception of a test start command form the tester, the control unit 12 executes the flicker sensitivity distribution measuring program stored beforehand in the storage unit 14 to display the fixation target a at a predetermined position on the screen 3 of the display 1 and to display the flickering target b on the screen 3 of the display 1. The control unit 12 displays video data received from the infrared television camera 7 in the fixation monitoring window 10c of the monitor picture 10a. When the control unit 12 receives a target perception signal from the target perception indicating device 9, the arithmetic unit 15 determines a flicker sensitivity on the bases of data on a high luminance and a low luminance in one cycle of flickering of the perceived flickering target. The control unit 12 executes control operations to display the flicker sensitivity determined by the arithmetic unit 15 at a position corresponding to the position of the target b in the display screen window 10e in the monitor picture 10a, to store the flicker sensitivity in the storage unit 14 and to write the flicker sensitivity to the recording medium loaded into the drive unit 16.

Figure 7:
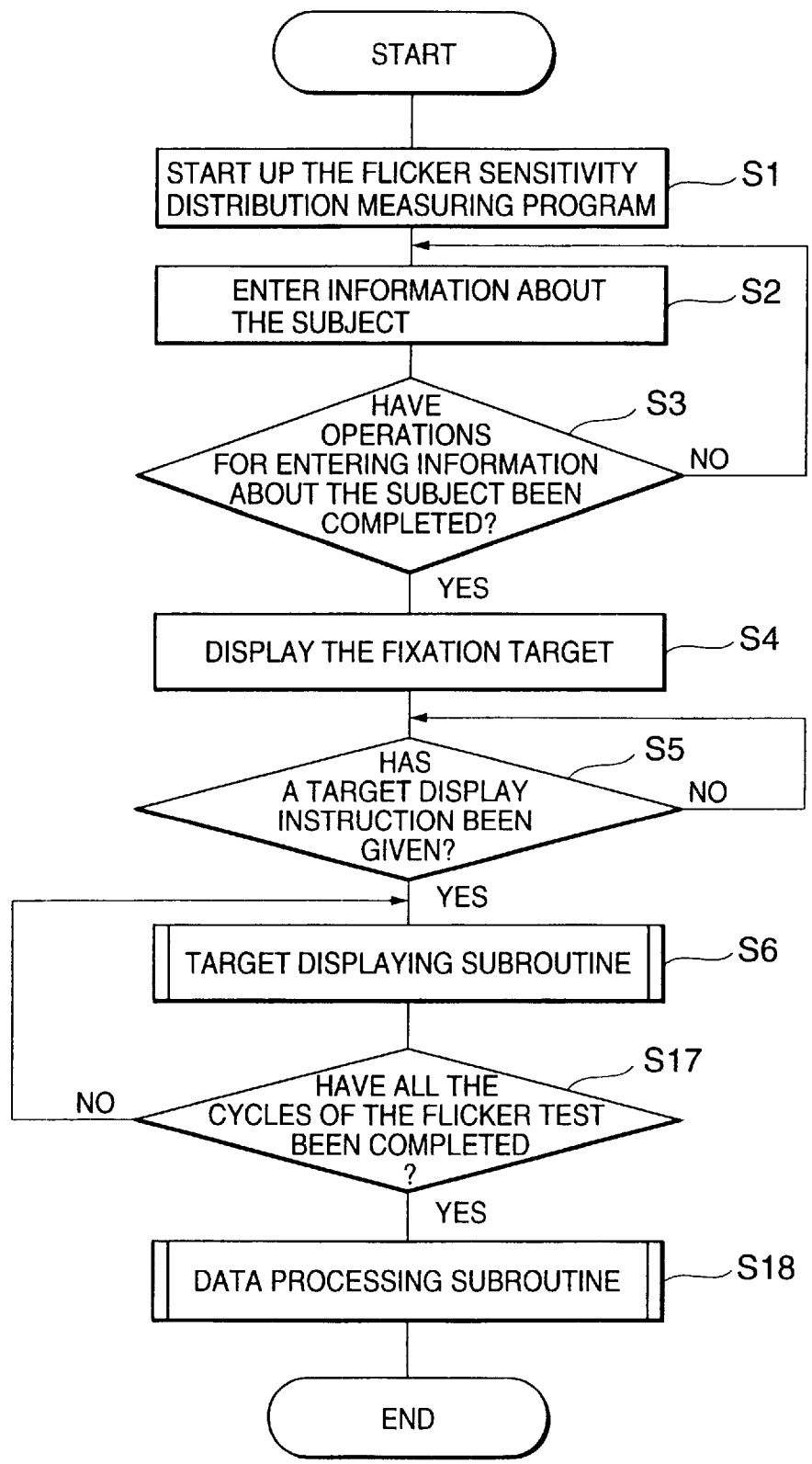
FIG. 7 is a flow chart of a flicker sensitivity distribution measuring program.
Figure 8:
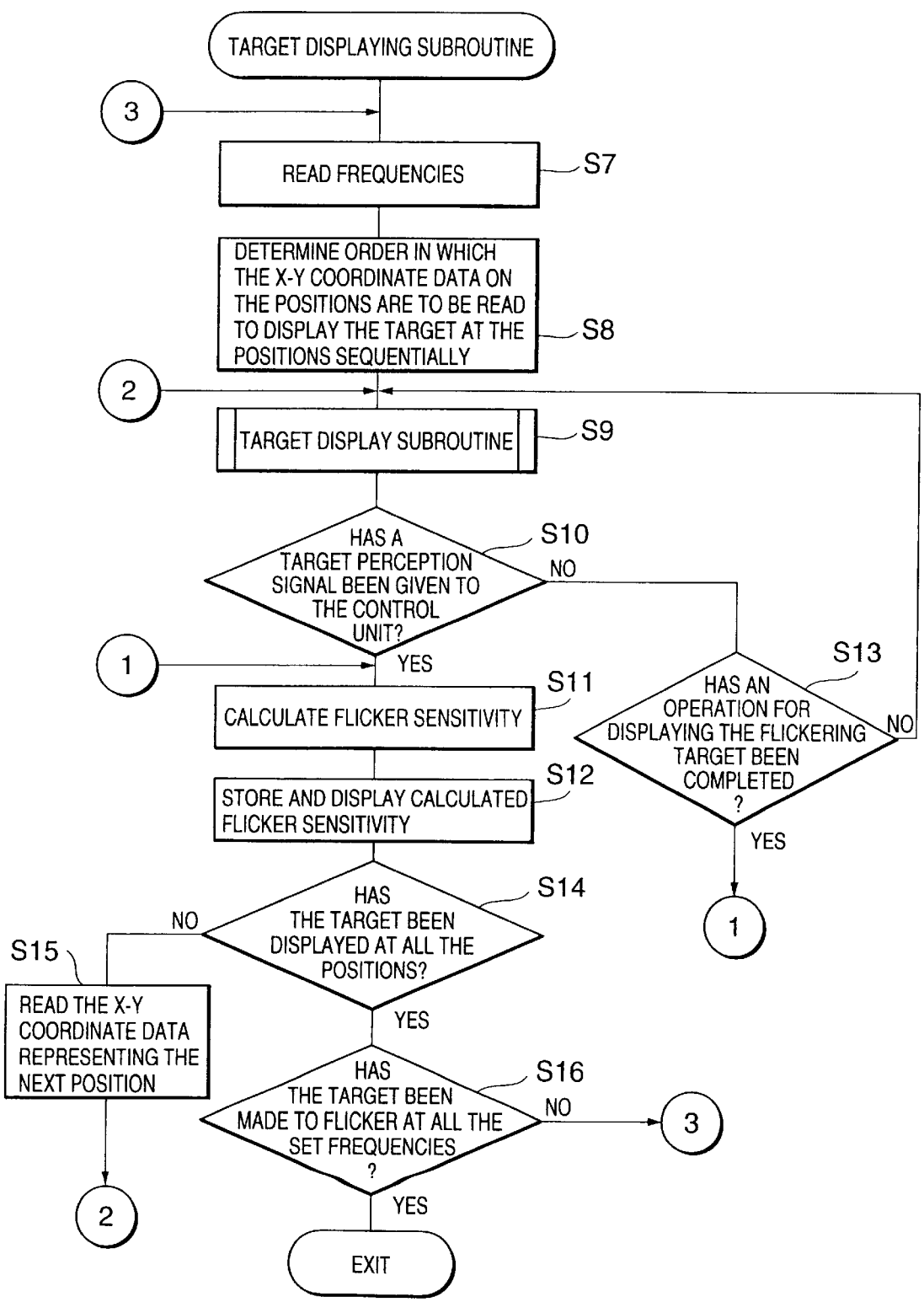
FIG. 8 is a flow chart of a displaying subroutine (step S6) included in the flicker sensitivity distribution measuring program shown in FIG. 7.
Figure 9A:
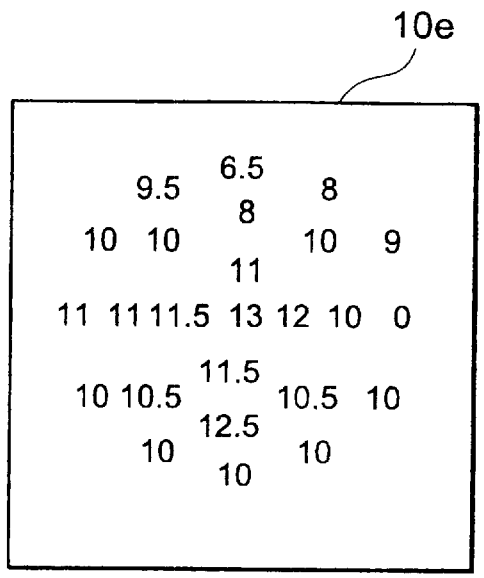
FIGS. 9A to 9D are views showing measured flicker sensitivity distributions determined through the measurement of the flicker sensitivities of subjects.
Figure 9B:
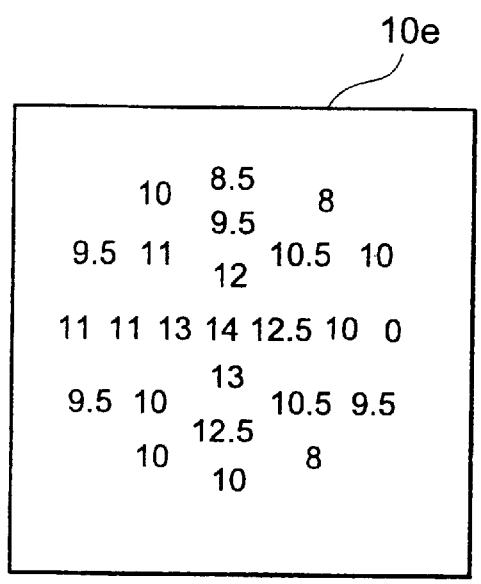
Figure 9C:
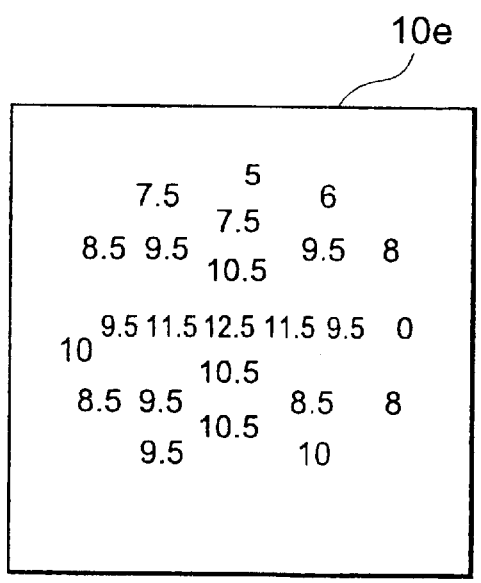
Figure 9D:
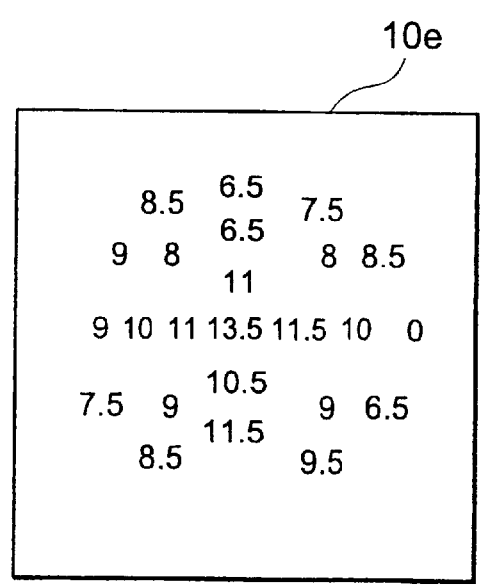

As shown in FIG. 4, the storage unit 14 has a position data memory (position data storing means) 14a, a sensitivity memory 14b, a frequency memory 14c, a luminance memory (luminance storing means) 14d, a program memory 14e and an information memory 14f. X-Y coordinate data as shown in FIG. 5A on positions c where the target b is to be displayed is stored in the position data memory (position data storing means) 14a. As shown in FIG. 5A, flicker sensitivities calculated on the basis of high luminances and low luminances of cycles of flickering of the target b perceived by the subject are stored in the sensitivity memory 14b in combination with the coordinate data stored in the position data memory 14a, respectively. As shown in FIG. 5B, a plurality of frequencies at which the target b is made to flicker are stored in the frequency memory 14c. As shown in FIG. 5C, luminance sets each of a high luminance $I_{max}$ and a low luminance $I_{min}$ in one cycle of flickering of the target b are stored in the luminance memory (luminance storing means) 14d. The luminance sets correspond to modulation factors including a minimum modulation factor representing a minimum flicker intensity to a maximum modulation factor representing a maximum flicker intensity, respectively. The luminance sets are stored in order of flicker intensity. The flicker sensitivity distribution measuring program specifying procedures shown in FIGS. 7 and 8 is stored in the program memory 14e. Information about the subject including a test number specifying the subject, subject's name, a subject's ID code, test date and test eye is stored in the information memory 14f.

The luminance I of the screen (background) 3 of the display 1 for displaying the target b is measured beforehand. The high luminance $I_{max}$ and the low luminance $I_{min}$ of each of the luminance sets stored in the luminance memory 14d are determined so as to meet a condition expressed by Expression (1).

$$(I_{max}+I_{min})/2=I \tag{1}$$

The arithmetic unit 15 generates random numbers specifying order in which the positions c are selected sequentially for displaying the target b, calculates a modulation threshold (referred to also as "threshold") on the basis of data on the luminance set of the high luminance $I_{max}$ and the low luminance $I_{min}$ in one cycle of flickering of the target b when the subject perceives the flickering target b, and calculates a flicker sensitivity on the basis of the calculated threshold.

More specifically, the threshold is determined on the basis of the luminance set of the high luminance $I_{max}$ and the low luminance $I_{min}$ in one cycle of flickering of the target b when the subject perceives the flickering target b by using Expression (2).

$$\text{Threshold } M=100\times(I_{max}-I_{min})/(I_{max}+I_{min}) \tag{2}$$

The value of the threshold M calculated by using Expression (2) is converted into a flicker sensitivity of a value in decibel (dB) by using Expression (3).

$$\text{Flicker sensitivity}=10\times\log(100/M) \tag{3}$$

The flicker sensitivity distribution measuring system may employ a personal computer, in which a main computer is employed as the controller 8, a CRT (cathode-ray tube) is employed as the display 1, a keyboard is employed as the operating unit 11, and a mouse is employed as the target perception indicating device 9.

Description will be given of a method of measuring flicker sensitivity distribution to be carried out according to the flicker sensitivity distribution measuring program by the flicker sensitivity distribution measuring system employing a personal computer with reference to FIGS. 7 and 8.

The subject sits on a chair opposite to the shading box 2, and fixedly sets the face in place with the chin resting on the chin support 5 and the forehead resting against the forehead support 6. The tester operates the operating unit (keyboard) 11 to start up the flicker sensitivity distribution measuring program stored in the program memory 14e of the storage unit 14 (step S1).

Subsequently, the tester enters Information about the subject including a test number specifying the subject, subject's name, subject's Id code, test date and test eye (step S2). A query is made in step S2 to see if operations for entering the information about the subject have been completed (step S3). Then, the fixation target a is displayed at the center of the screen 3 of the display (CRT) 1 as shown in FIG. 2 (step S4). In this state, the tester has the subject cover one of the subject's eyes and instructs the subject to fix the open eye on the fixation target a.

In a initial stage, only the fixation target a is displayed on the screen 3. The tester operates the operating unit (keyboard) 11 to enter a target display start signal (test start instruction) (step S5), and then the target b is made to flicker at a predetermined flickering speed (frequency) at a selected position c among the previously set positions c1 to c25 (step s6).

The target b is displayed by a procedure shown in FIG. 8. First, the control unit 12 reads the frequencies, such as 5 Hz, 10 Hz, 20 Hz and 30 Hz, from the frequency memory 14c of the storage unit 14 (step S7). Then, the arithmetic unit 15 generates random numbers, and determines order in which the X-Y coordinate data on the positions c1 to c25 are to be read to display the target b at the positions c1 to c25 sequentially (step S8). Subsequently, a first luminance set of a high luminance $I_{max}$ and a low luminance $I_{min}$ is read from the luminance memory 14d of the storage unit 14 to display the target b at a first position c, for example, the position c19, and the target b is made to flicker at the position c (position c19) (step S9). The target b is displayed by the method of limits of the ascending process, in which the target b is made to flicker at the selected frequency of, for example, 5 Hz at the position c first at luminances corresponding to the minimum modulation factor of 19 dB, and then the luminances are changed stepwise at a step corresponding to a modulation factor of 1 dB to luminances corresponding to the maximum modulation factor of 0 dB. The subject's eye is kept fixed at the fixation target a. Upon the perception of the flickering target b, the subject operates the target perception indicating device 9, i.e., clicks the mouse. The control unit 12 monitors the condition of the target perception indicating device 9 constantly to see whether or not a target perception indicating signal is given thereto. When the target perception indicating device (mouse) 9 is clicked to give a target perception signal to the control unit 12 (step S10), the arithmetic unit 15 reads data on the luminance set of the high luminance $I_{max}$ and the low luminance $I_{min}$ in one cycle of flickering of the target b displayed when the target perception signal is given, calculates a threshold M by using Expression (2), and converts the calculated threshold M into a flicker sensitivity of a value in decibel (step S11). The value in decibel representing the flicker sensitivity is stored in a storage area in the sensitivity memory 14e corresponding to the position c (position c19) where the perceived target b was displayed, and the value in decibel is displayed at a position (a position corresponding to the position c19) in the display screen window 10e (step S12). If it is decided in step S10 that any target perception signal is not received by the control unit 12, a query is made to see if an operation for displaying the flickering target b is completed (step S13). When the response in step S13 is negative, the routine jumps to step S9, the next luminance set of a high luminance $I_{max}$ and a low luminance $I_{min}$ is read from the luminance memory 14d, and the target b is made to flicker at the foregoing frequency (5 Hz) at the same position c (position c19). If it is decided in step S13 that the operation for making the target b flicker in all the luminance sets has been completed, it is decided that the target b displayed at the position c (position c19) could not be perceived by the subject, and a flicker sensitivity is calculated by the foregoing arithmetic method in step S11 on the basis of data on the luminance set in which the difference between the high luminance $I_{max}$ and the low luminance $I_{min}$ of one cycle of flickering of the target b is the greatest among those in all the luminance sets. Then, step S12 is executed and a query is made in step S14 to see if the target b flickering at the foregoing frequency (5 Hz) has been displayed at all the positions c. If the response in step S14 is negative, the X-Y coordinate data representing the next position (for example, a position c5) is read (step S15), the routine jumps to step S9 to display the target b at the new position. When it is decided in step S14 that the target b has been displayed at all the positions c, a query is made in step S16 to see if the target b has been made to flicker at all the set frequencies. If it is decided in step S16 that the target b has not been made to flicker at all the set frequencies, the routine jumps to step S7. If it is decided in step S16 that the target b has been made to flicker at all the set frequencies, a query is made in step S17 (FIG. 7) to see if the flicker test has been repeated by a predetermined number of cycles. The routine jumps to step S6 if the response in step S17 is negative. On the other hand, the data obtained by the flicker test is processed in step S18 and the flicker sensitivity distribution measuring program is ended if the response in step S17 is affirmative.

The tester monitors constantly the image of the eye formed by the infrared television camera 7 and displayed in the fixation monitoring window 10c (FIG. 3) to ensure that the fixation of the eye is maintained during the flicker test. The reliability of fixation is tested by testing the response of the eye to a stimulus given to the blind spot of Mariotte.

In the target displaying subroutine executed in step S6 of the flicker sensitivity distribution measuring program shown in FIG. 7, one cycle of the flicker test in which the target b is displayed at all the twenty-five positions. Two cycles of the flicker test may be carried out. If two cycles of the flicker test is executed, it is desirable to make reference to test results obtained by the first cycle of the flicker test and to display the target b only at some positions at which the target b needs to be displayed again for retesting so that the second cycle of the flicker test can be completed in a time shorter than that taken by the first cycle of the flicker test.

In the data processing subroutine executed in step S18 of the flicker sensitivity distribution measuring program shown in FIG. 8, a flicker sensitivity may be determined by calculating the arithmetic mean of test results obtained by an appropriate number of cycles of the flicker test.

It is desirable to store the test results in a text file on the hard disk or the like of the personal computer, to convert the text file into a data base file or a spreadsheet file for spreadsheet calculation when necessary to use the test results for database retrieval, statistical processing, graph plotting and data displaying in the future.

The flicker sensitivity distribution measuring system in this embodiment has the luminance memory 14d storing luminance sets of different luminance levels each of a high luminance $I_{max}$ and a low luminance $I_{min}$, the average of which is equal to the luminance I of the screen 3, i.e., the background of the target b, in one cycle of flickering of the target b; the position data memory 14a storing the coordinate data on the plurality of positions c on the screen 3 on which the target b is to be displayed; and the arithmetic unit 15 which determines a flicker sensitivity on the basis of the luminance set of a high luminance $I_{max}$ and a low luminance $I_{min}$ in one cycle of flickering of the target b displayed when the target perception signal is given by the target perception indicating device 9 upon the perception of the flickering target b by the subject. Also, the flicker sensitivity distribution measuring system in this embodiment reads the data on the luminance sets each of a high luminance $I_{max}$ and a low luminance $I_{min}$ in one cycle of flickering of the target b from the luminance memory 14d; displays the target b sequentially at the positions c on the screen 3 and makes the target b flicker in stepped flickering intensities. Therefore, the subject is unable to perceive the target b while the subject is unable to perceive the flicker of the target b. The subject is able to perceive the target b in the visual field only when the subject perceives the flickering target. Accordingly, the subject is able to maintain a fixation state easily and surely and hence the flicker sensitivity distribution can accurately be measured without making the subject tired.

This embodiment uses the computer of a configuration shown in FIG. 4 for measuring flicker sensitivity distribution. Therefore, the position of the target b on the screen 3 of the display 1 can easily be changed by changing the X-Y coordinate data representing the position c, and the flickering speed (frequency) of the target b, modulation factor, size, shape and luminance of the target b, and the luminance of the background can easily be changed. The modulation factor, the frequency and such can easily be changed with the average luminance of the target in one cycle of flickering kept equal to the luminance of the background. Accordingly, the measurement of flicker sensitivity distribution can very easily be automated.

The flicker sensitivity distribution measuring system in this embodiment employs the personal computer. The present invention may be embodied by a piece of special-purpose medical equipment.

Although the foregoing embodiment determines a flicker sensitivity by converting the threshold M into a corresponding value in decibel by using Expression (2), the flicker sensitivity may be the reciprocal of the threshold M.

Although the foregoing embodiment expresses one cycle of flickering of the target b by means of the luminance set of a high luminance $I_{max}$ and a low luminance $I_{min}$, one cycle of flickering of the target b may be expressed by means of three or more different luminances. The target b may be modulated by any one of suitable modulating techniques including a rectangular wave modulation technique, a trapezoidal wave modulation technique, a sinusoidal wave modulation technique and a triangular wave modulation technique. When any one of those modulation techniques is used, the average luminance can easily be determined by integration.

Although the foregoing embodiment adjusts the brightness of the screen 3 of the CRT after connecting the CRT to a power source and displays the target on the gray background in a monochromatic flickering point because the conventional flicker tests generally use white light, a target of any suitable color matching the color of the background may be used.

In the foregoing embodiment, the flicker sensitivity distribution measuring program specifying the procedures shown in FIGS. 7 and 8 to be executed by the computer may be recorded on a recording medium capable of being used for data entry to a computer, such as a floppy disk, a MO (magneto optical) disk, a CD-ROM (compact disk read only memory) or a CD-R (compact disk-recordable). Stored in the recording medium, in addition to a program file containing the flicker sensitivity distribution program specifying the procedures shown in FIGS. 7 and 8, are a position data file containing X-Y coordinate data representing the positions c where the target b is to be displayed, a frequency file containing a plurality of frequencies specifying flickering speeds of the target b, and a luminance file containing the luminance sets each of a high luminance $I_{max}$ and a low luminance $I_{min}$ correspond to modulation factors including a minimum modulation factor representing a minimum flicker intensity to a maximum modulation factor representing a maximum flicker intensity, respectively. When measuring flicker sensitivity distribution, the recording medium is loaded into the drive unit 16 of the computer shown in FIG. 4, the flicker sensitivity distribution measuring program is loaded into the program memory 14e of the storage unit 14, the X-Y coordinate data contained in the position data file is loaded into the position data memory 14a, the frequencies contained in the frequency file are loaded into the frequency memory 14c, the luminance sets each of a high luminance $I_{max}$ and a low luminance $I_{min}$ contained in the luminance file are loaded into the luminance memory 14d, and the flicker sensitivity distribution measuring program stored in the program memory 14e is actuated for the measurement of flicker sensitivity distribution.

Accurate tests can easily be achieved by measurement at home, mass survey at school, and screening tests by testers not having expert knowledge of clinical ophthalmology by using the recording medium storing the flicker sensitivity distribution measuring program. The flicker sensitivity distribution measuring program can be produced by using the authoring tool or C which operates under the MAC OS® of Apple Computer Inc. or the Windows 95® of Microsoft Corp., which expands the range of utilization of the flicker sensitivity distribution measuring program.

Only the program file may be stored in the computer-readable recording medium storing the flicker sensitivity distribution measuring program, and data files including the position data file, the frequency file and the luminance file may be stored in another recording medium. Data contained in the data files may be changed according to test conditions. The results of the test of each subject may be written to a recording medium, and the personal computer may read information about the subject, and data on the results of the previous tests of the subject before conducting flicker sensitivity distribution measurement.

The present invention is not limited in its practical application to the embodiment described above and many modifications thereof are possible without departing from the scope of the invention. For example, although the foregoing embodiment displays the target by the method of limits, the target may be displayed by any suitable method, such as an up-and-down method, a constant method or a method of adjustment. (Refer to Hideko Fukuda and Kazutaka Kani, "Shikiichi to sono Sokutei-hou", Shinkei Ganka 7, pp. 291–298 (1990) for a method of limits, an up-and-down method, a constant method and a method of adjustment.)

An example of the foregoing embodiment will be described below with reference to FIGS. 9A to 9D.

FIGS. 9A to 9D are diagrams showing flicker sensitivity distributions produced by using test data obtained through the actual test of a healthy subject. These diagrams are displayed in the display screen window 10e (FIG. 3) of the monitor picture 10a displayed on the monitor display 10. The test data on the flicker sensitivity distributions shown in FIGS. 9A, 9B, 9C and 9D was obtained through tests in which the target was made to flicker at 5 Hz, 10 Hz, 20 Hz and 30 Hz, respectively. Positions where the flicker sensitivity is 0 dB corresponds to the subject's blind spot of Mariotte. The flicker sensitivity distribution measuring program was produced by using an authoring tool which operates under the MAC OS®.

The flicker sensitivity distribution measuring system employed a personal computer, and a target was made to flicker on the screen 3 of a display (CRT) 1. The target was a square mark of a target size of 60' (visual angle) for a distance of 25 cm between the screen 3 and the test eye (square having equal sides of 4.5 mm on the screen 3). The luminance of the screen (background) 3 of the display (CRT) 1 was 45 cd/m². The target was made to flicker in the following luminance sets each of (high luminance $I_{max}$, low luminance $I_{min}$).

Luminance sets ($I_{max}$, $I_{min}$) (cd/m²)

| | | | | |
|---|---|---|---|---|
| (90, 0.1) | (81, 9) | (74, 16) | (68, 23) | (63, 27) |
| (59, 31) | (56, 34) | (54, 36) | (52, 38) | (51, 39) |
| (50, 41) | (49, 41) | (48, 42) | (47.3, 42.8) | (46.8, 43.2) |
| (46.4, 43.7) | (46.1, 43.9) | (45.9, 44.1) | (45.8, 44.3) | (45.6, 44.4) |

These luminance sets each of a high luminances $I_{max}$ and a low luminances $I_{min}$ correspond to the following modulation factors. Modulation factors (dB)

| | | | | |
|---|---|---|---|---|
| 0 | 1 | 2 | 3 | 4 |
| 5 | 6 | 7 | 8 | 9 |
| 10 | 11 | 12 | 13 | 14 |
| 15 | 16 | 17 | 18 | 19 |

First the target was made to flicker at the frequencies (5 Hz, 10 Hz, 20 Hz, 30 Hz) and at luminances corresponding to the minimum modulation factor of 19 dB at an optional position c on the screen 3 of the display (CRT) 1 by the method of limits of the ascending process. The luminances were changed stepwise at a step corresponding to a modulation factor of 1 dB to luminances corresponding to the maximum modulation factor of 0 dB. If the visual function of the subject is abnormal, the value approximately equal to 0 dB is displayed at a corresponding position in the display screen window 10e.

What is claimed is:

1. A flicker sensitivity distribution measuring system comprising:

a stand for fixedly holding a face of a viewer;

a display having a screen facing the stand;

a controller for controlling the display to display a flickering target on the screen of the display and determining a flicker sensitivity of the viewer when the flickering target is perceived by the viewer; and a target perception indicating unit which provides a target perception signal representing perception of the flickering target;

wherein the controller comprises a luminance data storing means storing different sets of luminance values, each set comprising a high luminance value Imax and a low luminance value Imin, wherein for each set, the average of Imax and Imin is equal to the luminance of the screen serving as a background of the flickering target;

a position data storing means storing a plurality of sets of coordinates indicating positions for the flickering target; and an arithmetic means for determining a flicker sensitivity on the basis of the high luminance value Imax and the low luminance value Imin in one cycle of flickering upon reception of the target perception signal, and wherein in each cycle of flickering, the controller:

reads one set of luminance values, comprising the high luminance value Imax and the low luminance value Imin, from the luminance data storing means;

reads one set of coordinates indicating a position for the flickering target from the position data storing means;

displays the flickering target at the indicated position on the screen; and changes the luminance of the flickering target between the high luminance value Imax and the low luminance value Imin.

2. The flicker sensitivity distribution measuring system according to claim 1, wherein the flicker sensitivity is determined by calculating a modulation threshold on the basis of the high luminance value $I_{max}$ and the low luminance value $I_{min}$ in one cycle of flickering and converting the modulation threshold into a value in decibels.

3. The flicker sensitivity distribution measuring system according to claim 2, wherein the modulation threshold $M=100\times(I_{max}-I_{min})/(I_{max}+I_{min})$; and the flicker sensitivity=$10\times\log(100/M)$.

4. The flicker sensitivity distribution measuring system according to claim 1, further comprising:

an image pickup device for forming an image of the face of the viewer; and a monitor display for monitoring fixation of an eye of the viewer through observation of the image formed by the image pickup device.

5. The flicker sensitivity distribution measuring system according to claim 1, wherein an operating unit and the target perception indicating unit are included in a personal computer.

* * * * *